(12) United States Patent
Trainor et al.

(10) Patent No.: US 10,488,398 B2
(45) Date of Patent: Nov. 26, 2019

(54) CHEMICAL IMPAIRMENT DETECTION SYSTEM WITH AN INTEGRATED, MULTI-FUNCTION BREATH CHAMBER

(71) Applicant: #1A LifeSafer, Inc., Cincinnati, OH (US)

(72) Inventors: Nicholas M. Trainor, Wake Forest, NC (US); Louis Urani, Morrisville, NC (US); James Hu, Raleigh, NC (US); Jeffrey Vatter, Raleigh, NC (US); Scott A. Galvin, Chapel Hill, NC (US); David Hamo, Raleigh, NC (US); William H. Collins, Cary, NC (US); James Dunn, Raleigh, NC (US)

(73) Assignee: #1 A LifeSafer, Inc., Blue Ash, OH (US)

( * ) Notice: Subject to any disclaimer, the term of this patent is extended or adjusted under 35 U.S.C. 154(b) by 84 days.

(21) Appl. No.: 14/973,275

(22) Filed: Dec. 17, 2015

(65) Prior Publication Data

US 2017/0176411 A1    Jun. 22, 2017

(51) Int. Cl.
*G01N 33/497* (2006.01)
*B60K 28/06* (2006.01)

(52) U.S. Cl.
CPC ......... *G01N 33/4972* (2013.01); *B60K 28/06* (2013.01); *B60K 28/063* (2013.01); *G01N 33/497* (2013.01)

(58) Field of Classification Search
CPC .. G01N 33/497; G01N 33/4972; B60K 28/06; B60K 28/063
USPC .......................................... 73/23.3; 600/543
See application file for complete search history.

(56) References Cited

U.S. PATENT DOCUMENTS

| 4,132,109 A | 1/1979 | VanderSyde |
| 4,163,383 A | 8/1979 | VanderSyde et al. |
| 4,678,057 A | 7/1987 | Elfman et al. |
| 4,697,666 A | 10/1987 | Collier et al. |
| 4,738,333 A | 4/1988 | Collier et al. |

(Continued)

FOREIGN PATENT DOCUMENTS

| EP | 2127599 A1 | 12/2009 |
| EP | 2163381 A1 | 8/2014 |

(Continued)

OTHER PUBLICATIONS

European Search Report issued from European Patent Application No. 16205130.4, dated Jul. 20, 2017, 16 pp., European Patent Office, The Hague, Netherlands.

*Primary Examiner* — Peter J Macchiarolo
*Assistant Examiner* — Irving A Campbell
(74) *Attorney, Agent, or Firm* — Wood Herron & Evans LLP

(57) ABSTRACT

A chemical impairment detection system adaptable for use in a vehicle. The impairment detection system includes an intake adapted to receive an air sample from a source and an alcohol sensor for detecting an alcohol level in the air sample. An integrated breath chamber channels the air sample from the intake to the alcohol sensor. Source evaluator means in the breath chamber measure one or more characteristics of the received air sample for validating the sample. The source evaluator means measures the air sample characteristics as the air sample flows through the breath chamber.

27 Claims, 11 Drawing Sheets

(56) References Cited

U.S. PATENT DOCUMENTS

| | | |
|---|---|---|
| 4,809,810 A | 3/1989 | Elfman et al. |
| 4,843,377 A | 6/1989 | Fuller et al. |
| 4,900,514 A | 2/1990 | Fuller |
| 4,914,038 A | 4/1990 | Jewitt |
| 4,916,435 A | 4/1990 | Fuller |
| 4,996,161 A | 2/1991 | Conners et al. |
| 4,999,613 A | 3/1991 | Williamson et al. |
| 5,426,415 A | 6/1995 | Prachar et al. |
| 5,734,090 A | 3/1998 | Koppel et al. |
| 6,026,674 A | 2/2000 | Gammenthaler |
| 6,167,746 B1 | 1/2001 | Gammenthaler |
| 6,726,636 B2 | 4/2004 | Der Ghazarian et al. |
| 6,748,792 B1 | 6/2004 | Freund et al. |
| 6,853,956 B2 | 2/2005 | Ballard, Jr. et al. |
| 6,923,040 B2 | 8/2005 | Stock |
| 6,956,484 B2 | 10/2005 | Crespo |
| 6,967,581 B2 | 11/2005 | Karsten |
| 7,171,842 B2 | 2/2007 | Stock et al. |
| 7,204,335 B2 | 4/2007 | Stewart et al. |
| 7,256,700 B1 | 8/2007 | Ruocco et al. |
| 7,311,665 B2 | 12/2007 | Hawthorne et al. |
| 7,341,693 B2 | 3/2008 | Der Ghazarian et al. |
| 7,400,258 B2 | 7/2008 | Crespo |
| 7,413,047 B2 | 8/2008 | Brown et al. |
| 7,422,723 B1 | 9/2008 | Betsill |
| 7,451,852 B2 | 11/2008 | Stewart et al. |
| 7,462,149 B2 | 12/2008 | Hawthorne et al. |
| 7,541,192 B2 | 6/2009 | Stock |
| 7,603,886 B2 | 10/2009 | Stock |
| 7,603,887 B2 | 10/2009 | Schlichte |
| 7,611,461 B2 | 11/2009 | Hawthorne et al. |
| 7,616,123 B2 | 11/2009 | Ridder et al. |
| 7,641,611 B2 | 1/2010 | Hawthorne et al. |
| 7,671,752 B2 | 3/2010 | Sofer |
| 7,768,380 B2 | 8/2010 | Breed et al. |
| 7,823,681 B2 | 11/2010 | Crespo et al. |
| 7,833,166 B2 | 11/2010 | Ruffert |
| 7,934,577 B2 | 5/2011 | Walter et al. |
| 7,993,281 B2 | 8/2011 | Stock et al. |
| 8,059,003 B2 | 11/2011 | Roth |
| 2002/0127145 A1 | 9/2002 | Der Ghazarian et al. |
| 2003/0176803 A1 | 9/2003 | Gollar |
| 2003/0183437 A1 | 10/2003 | Mendoza |
| 2004/0138823 A1 | 7/2004 | Gollar |
| 2005/0223774 A1* | 10/2005 | Stock ............... G01N 33/497 73/23.3 |
| 2006/0173256 A1 | 8/2006 | Ridder et al. |
| 2006/0202838 A1 | 9/2006 | Hawthorne et al. |
| 2007/0120691 A1 | 5/2007 | Braun |
| 2008/0170762 A1 | 7/2008 | Endo et al. |
| 2008/0227466 A1 | 9/2008 | Rabanne et al. |
| 2009/0053110 A1 | 2/2009 | Chang et al. |
| 2009/0169068 A1 | 7/2009 | Okamoto |
| 2009/0293589 A1 | 12/2009 | Freund et al. |
| 2009/0325639 A1 | 12/2009 | Koehn |
| 2010/0012417 A1* | 1/2010 | Walter ............. B60K 28/063 180/272 |
| 2010/0060465 A1* | 3/2010 | Stetter ............. B81B 3/0021 340/584 |
| 2010/0251804 A1 | 10/2010 | Morley et al. |
| 2010/0268425 A1 | 10/2010 | Pettersson et al. |
| 2010/0274411 A1 | 10/2010 | Ozaki |
| 2010/0294583 A1 | 11/2010 | Biondo et al. |
| 2010/0314190 A1 | 12/2010 | Zimmermann et al. |
| 2011/0015873 A1 | 1/2011 | Iiams et al. |
| 2011/0057800 A1 | 3/2011 | Sofer |
| 2011/0079073 A1 | 4/2011 | Keays |
| 2011/0084820 A1 | 4/2011 | Walter et al. |
| 2011/0178420 A1 | 7/2011 | Ridder et al. |
| 2011/0193708 A1 | 8/2011 | Comeau |
| 2013/0305808 A1* | 11/2013 | Yoo ............... G01N 33/4972 73/23.3 |
| 2015/0204844 A1* | 7/2015 | Nothacker ....... G01N 33/4972 73/23.3 |
| 2015/0355161 A1* | 12/2015 | Takeuchi ........... G01N 33/497 73/23.3 |
| 2016/0146780 A1* | 5/2016 | Granstam ............ G01N 33/98 73/23.3 |

FOREIGN PATENT DOCUMENTS

| | | | |
|---|---|---|---|
| GB | 1512587 A * | 6/1978 | ......... G01N 33/4972 |
| GB | 2139387 A | 11/1984 | |
| WO | 199222813 A1 | 12/1992 | |
| WO | 2013 191633 A1 | 12/2013 | |

* cited by examiner

CHEMICAL IMPAIRMENT DETECTION SYSTEM WITH AN INTEGRATED, MULTI-FUNCTION BREATH CHAMBER

FIELD OF THE INVENTION

The present invention relates to chemical impairment detection devices and, more particularly, to obtaining accurate assessments from impairment detection devices while deterring and identifying circumvention.

BACKGROUND OF THE INVENTION

The operation of motor vehicles by individuals who are chemically impaired by alcohol or another substance is a major safety problem. Many vehicle accidents involve someone that is under the influence of alcohol and, in some cases, individuals who have already been cited or otherwise identified as misusing or abusing alcohol. In addition to putting the impaired driver at an increased risk of injury or death, the operation of a vehicle while under the influence of alcohol often also affects the safety of others, such as the drivers and passengers in other vehicles. In addition to the increased risk of serious bodily injury or death caused by someone who is driving while under the influence of a chemical substance, there is also an increased risk of serious damage to personal and real property, as well as the cost and potential distraction from other needed services associated with the law enforcement and rescue workers that are called upon to respond to such accidents. As used herein, the term vehicle is intended to include any device or structure for transporting persons or things including, without limitation, automobiles, trucks, boats, planes, trains, etc.

Recognizing the seriousness of driving while under the influence, many laws have been written prohibiting such conduct, and providing various methods for dealing with such offenses when they occur. For example, a court or licensing authority may suspend the driving privileges of someone who is convicted of driving while under the influence of alcohol, or may require that a chemical impairment detection device, such as a BAIID (breath alcohol ignition interlock device), be installed in his or her vehicle. Additionally, a state may require repeat offenders to install such devices as a condition of having their license reinstated. Chemical impairment detection devices may also be used in non-vehicular applications to monitor and detect whether someone has improperly or without authorization consumed alcohol or drugs. For example, abstinence from the use of any alcohol may be a condition of a repeat offender's parole, probation, or home confinement.

When an impairment detection and ignition interlock device, also known as a sobriety interlock, is installed in an individual's vehicle, the individual must pass a sobriety test before the vehicle can be started. However, since the use of impairment detection interlocks is normally done outside the presence of law enforcement or any other supervising authority, and since a penalty may be attributed to a failed test, e.g., the vehicle will not start and a condition of parole may be violated, there can be a temptation to tamper with the impairment detectors to attempt to fraudulently affect its results. For example, if the designated tester has been drinking, he or she could ask someone who is sober to take the test for them. Alternatively, an air compressor, balloon, or other like source of forced air may be blown into a sampling device in an attempt to circumvent the interlock. Once such a clean sample is provided, and the vehicle starts, the impaired driver can then drive away. To prevent this from occurring, detection devices need to provide protection against circumventing the device. In particular, it is important to verify that the exhaled breath sample used in the sobriety test is indeed provided by the designated tester.

To validly determine a tester's blood-alcohol content (BAC) from his or her breath, impairment detection devices typically require a "deep-lung" breath sample. In particular, most state laws require a deep lung air sample having a minimum flow volume of 1.2-1.5 liters of air. During such a sample, the air blown into the mouthpiece generally must comprise alveolar air, which occurs when an expiratory breath substantially exhausts the lungs. Breath expired from the upper portions of the respiratory tract does not necessarily have an alcohol level proportional to that of the bloodstream, and could provide an inaccurate reading. Therefore, the breath-sampling or detection system should detect and prevent the processing of shallow exhalations, e.g., when a tester blows only short puffs of air from the upper portions of the respiratory tract. Additionally, impairment detection devices often require a tester to hum as air is expelled from the lungs, in order to verify that the air sample is from a human and not a forced air source. Typically, a tester is required to blow and hum for about 5 seconds in order to substantially exhaust the lungs and provide a deep-lung sample.

Impairment detection devices perform pressure measurements of an expiratory breath sample to ensure that the sample contains the minimum fluid volume required by law. These measurements have typically been accomplished using differential pressure sensors in combination with an amplifier. This measurement scenario has required a number of components, tubing, and gaskets to properly feed the air sample from the air intake tube to the pressure sensors, adding to the cost and complexity of the detection device. This diversion of sample air away from the breath chamber also increases the likelihood of sample air leaking within the device, reducing the ability to measure pressure accurately, and creating a need to use protective coatings on electronic components and printed circuit boards to prevent degradation due to breath condensation.

External moisture and condensation from breath samples can affect the operation and longevity of a detection device. Because these devices are designed to be used before a vehicle is started, in extremely cold weather an impairment detection device will oftentimes be very cold during its initial use. Breathing warm air into a cold device in an attempt to start a vehicle can cause undesirable breath condensation within the device. This condensation can affect the accuracy of the alcohol sensor, leading to a false positive or negative result.

Accordingly, to overcome the above-described problems in impairment detection devices, it is desirable to have an impairment detection device that uses a simplified, low-cost pressure sensor for more accurately measuring the volume of a breath sample. Additionally, it is desirable to have an impairment detection device that can be preheated in cold environments, prior to receiving a breath sample, to prevent breath moisture condensation and promote optimum operation and accuracy of the device. Further, it is desirable to have a device which includes air-tight seals around a breath intake chamber to prevent breath sample air from leaking within the device. Furthermore, it is desirable to have an impairment detection device that detects a hum sound associated with the intake of a breath sample. Additionally, it is desirable to integrate measuring the volume of an air sample, temperature sensing, and hum detection into a unitary breath chamber.

SUMMARY OF THE INVENTION

The present invention addresses the shortcomings of the prior art by improving a chemical impairment detection system in accordance with several different aspects.

In a first aspect, the invention comprises a chemical impairment detection system for use in a vehicle. The impairment detection system includes an intake adapted to receive an air sample and an alcohol sensor for detecting an alcohol level in the air sample. An integrated breath chamber having a cavity formed therein channels the air sample from the intake to the alcohol sensor. Source evaluator means are associated with the breath chamber for analyzing one or more characteristics of the air sample in the chamber for validating the sample. The source evaluator means analyzes the air sample as the sample is blown through the chamber. The system further comprises a lockout means for disabling an ignition of the vehicle if the source evaluator means determines the air sample is an invalid sample.

In a second aspect, the invention features an integrated breath chamber assembly for an alcohol impairment detection device having an air sample intake and an alcohol sensor. The assembly includes a breath chamber having a cavity formed therein for receiving and evaluating an air sample. The cavity extends between the intake and the alcohol sensor for channeling an air sample from the intake to the sensor. Pressure sensing means in the cavity measure the pressure of the air sample in the cavity. A processing means applies an algorithm to the pressure measurements to calculate a breath sample volume. The processing means invalidates the air sample if the breath sample volume is below a minimum threshold volume. The processing means also invalidates the breath sample if the pressure of the blown air sample is too high, indicating that the tester is blowing too hard, or too softly, indicating that the tester is not blowing in an acceptable or appropriate manner.

In a third aspect, the present invention provides a chemical impairment detection device having an intake adapted to receive an air sample from a source, and an alcohol sensor for detecting an alcohol level in the air sample. An integrated breath chamber receives the air sample and channels the air sample from the intake to the alcohol sensor. The breath chamber includes a temperature measuring means for measuring temperature in the breath chamber, a pressure sensing means for measuring air sample pressure, and an audio detector for detecting sound waves associated with the air sample. A processing means receives signals from one or more of the temperature sensing means, pressure sensing means, and audio detector, and determines the validity of the air sample. The processing means can disable operation of an associated vehicle when the received air sample is determined to be invalid.

The above and other objects and advantages of the present invention shall be made apparent from the accompanying drawings and the description thereof.

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Figure 1:
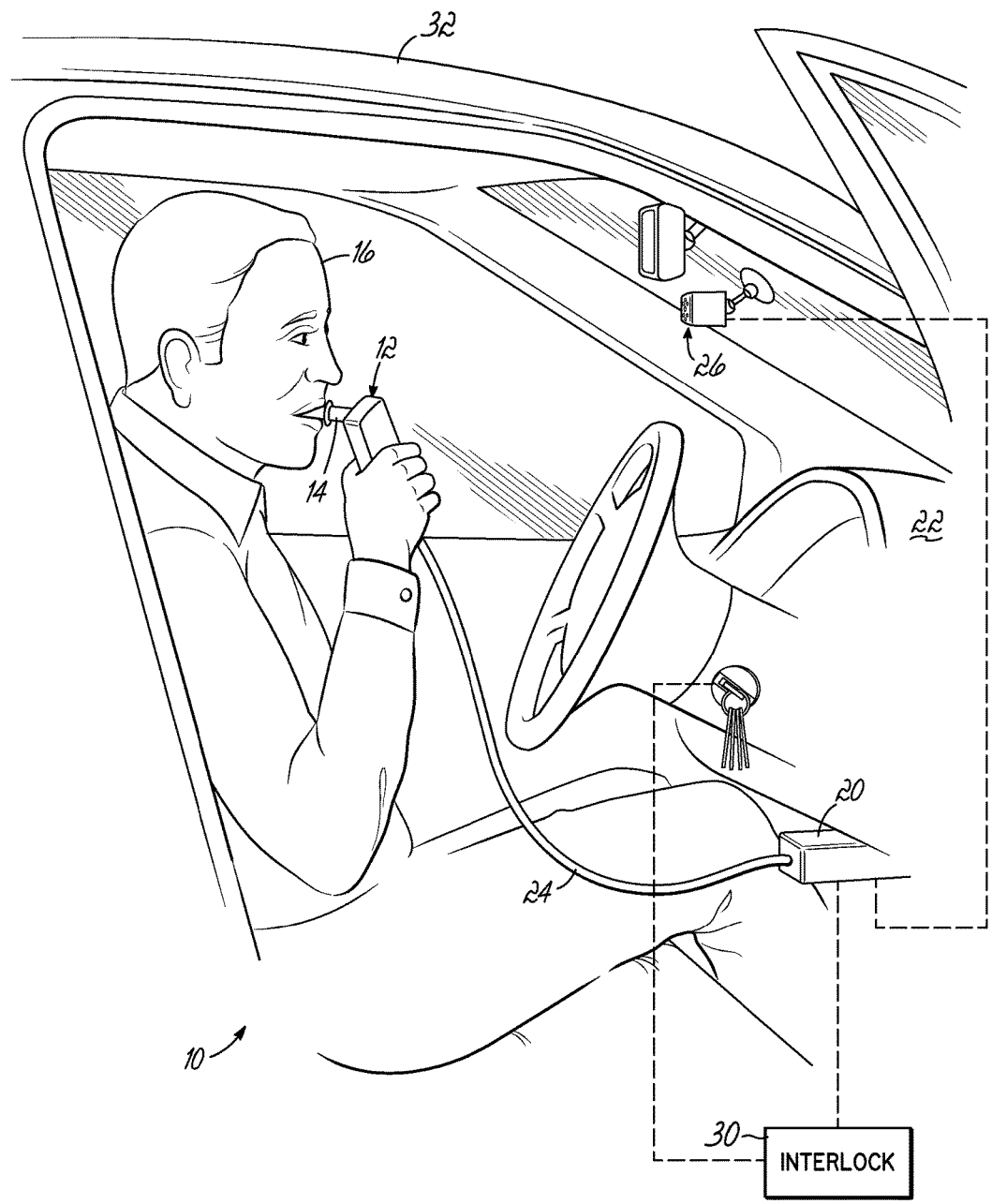
FIG. 1 is a perspective view of an embodiment of a chemical impairment detection system according to the present invention.

FIG. 1 illustrates an exemplary embodiment of a chemical impairment detection system 10. In this embodiment, system 10 is shown as having a hand-held device 12 for receiving and analyzing the alcohol content of one or more air samples. Hand-held device 12 includes an intake member for receiving an air sample, such as a tester's 16 breath sample. The intake member can include a mouthpiece 14 for facilitating input of the breath sample. The mouthpiece 14 may be disposable and can be configured so as to be required to be locked in the device 12 before a test can be taken. The mouthpiece 14 may also be constructed of a material, such as hard plastic, that will be resistant to bending.

When installed in a vehicle, the hand-held device 12 is typically connected to a control/relay module (CRM) 20, generally located under the dashboard 22, via a coiled cord 24. The hand-held unit 12 and relay module 20 will typically operate between −40° C. to 85° C. and between 10% to 95% relative humidity. Device 12 can be powered from the vehicle electrical harness through cord 24. Alternatively, the device can include a battery or other self-contained power source.

System 10 also may include a system 26 that provides video surveillance and communication capabilities. System 26 may include a camera positioned and adapted to have a camera angle that captures the identifying facial features of the tester 16. By capturing a facial image of the tester 16, the system 26 aids in confirming the identity of the tester, and deters fraudulent sampling or circumvention of the system. The system 26 may capture at least a portion of the hand-held sampling device 12 and mouthpiece 14 to positively link the impairment sample received and analyzed with the impairment tester 16. Additional details of a video surveillance system for use with an impairment detection device can be found in commonly-assigned U.S. Pat. No. 8,359, 901, which is incorporated herein by reference.

System 26 may also include a wireless communication transceiver, e.g. cellular telephone, enabling two-way communication. The communication transceiver may communicate with an external receiver to facilitate the transfer of a chemical impairment detection test result and the facial image of the tester to an external receiver, such as a monitoring facility. Additionally, the wireless communication transceiver may be used by the monitoring facility to dynamically order a recall of the system 10, or to lock the ignition in response to a violation. The wireless transceiver may also be used to provide an override of system 10, such as when the system has been locked out due to an infraction, such as a missed service interval window. An authorization can be communicated via system 26 to allow the tester 16 to blow a test sample and perform limited operation of the vehicle, such as driving the vehicle to a monitoring facility or other designated location. Additionally, the communication transceiver can be used to authorize a bypass of the system 10 for a set period of time, such as to allow servicing of the vehicle by a mechanic. A system 10 with a wireless communication transceiver could also be used by a monitoring facility to dynamically request random alcohol tests or to otherwise communicate with the system or tester 16.

The chemical impairment detection system 10 may further comprise a test window alert, which may be in the form of audio, visual, or motion alerts, or some combination thereof, which can be communicated through the system 26, to alert the tester 16 of a time window during which the chemical impairment detection test must be commenced. A global positioning system (GPS) may also be included within the system 26 to record the location of the vehicle 32 such as when a violation occurs. Recording and/or communicating GPS coordinates may provide corroborating evidence of the tester's 16 identity, e.g., if the location happens to be in the tester's 16 garage, or may provide useful geographical information for legal jurisdictional purposes. Using the GPS capability, law enforcement could be dispatched to the location of the vehicle 32 when there is a failed test. This capability could be extremely beneficial to intercept someone who is driving while impaired. When used in vehicular applications, system 10 may include a vehicle ignition interlock 30 that is in operable communication with the hand-held device 12. Ignition interlock 30 can be instructed by hand-held device 12 to prevent operation of the vehicle, such as when the device detects an invalid breath sample or a failed impairment test. The video surveillance, communication and GPS functions can be combined in one system as shown. Alternatively, each of the functions could be provided as separate modules within system 10. Additional components, known in the industry, can be added to the system 10 to provide for added capabilities.

Figure 2:
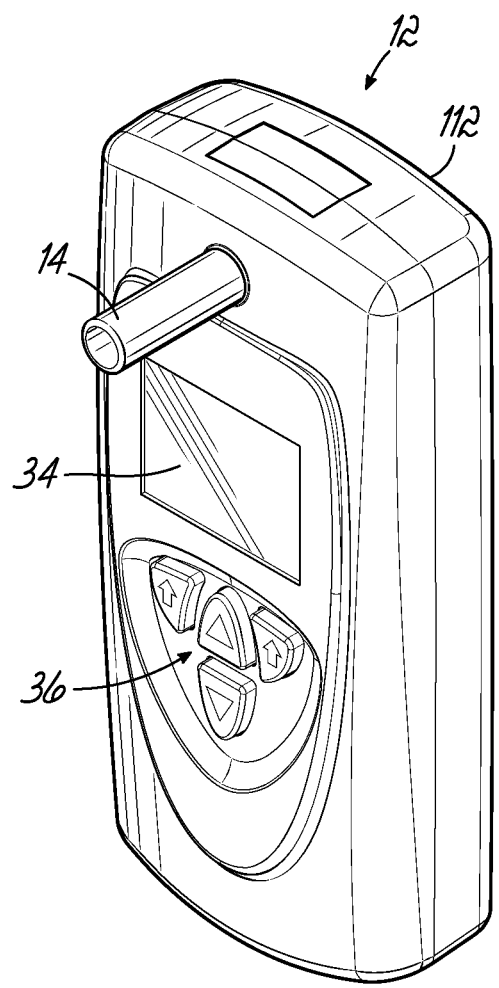
FIG. 2 is an isometric view of an embodiment of a hand-held device for the chemical impairment detection system shown in FIG. 1.

The hand-held device 12 and system 26 may contain one or more LED's for communication with a designated tester 16. As shown in FIG. 2, device 12 may also include a display 34 for communicating prompts, instructions, results, etc. to the tester 16. A keypad 36 or other input device can be provided for enabling the tester 16 to enter data, or respond to commands or prompts of the device. Hand-held device 12 may also include a speaker 102, shown in FIG. 3, for providing audio prompts, instructions, test results, or otherwise communicating with the tester. For example, the device 12 may beep during a testing window as an indication that the tester 16 is to continue blowing until the beeping stops. Or, device 12 may direct the tester 16 to blow harder or softer, hum louder, or otherwise provide directions to facilitate obtaining a proper breath sample from the tester 16. A microprocessor 40 and memory 42 are also included within the device 12 to log event information and provide various programmable options to determine device functionality.

Turning now to FIGS. 3-8, which depict a first exemplary embodiment of an integrated breath chamber assembly 50 for impairment detection system 10. As will be described below, assembly 50 is a multi-functional unit integrated within hand-held device 12 for channeling a breath sample from mouthpiece 14 to an alcohol sensor 60. Assembly 50 includes a one-piece, injection-molded housing 52 having a breath chamber cavity 54 formed therein. Housing 52 includes an air intake opening 56. Mouthpiece 14 is shaped for insertion into opening 56 for inputting a breath sample into cavity 54. Chamber cavity 54 is shaped for receiving the breath sample and channeling the sample to an alcohol sensor 60, as indicated by arrows 58 in FIGS. 6 and 8. In the exemplary embodiment, alcohol sensor 60 is an electrochemical fuel cell sensor. In addition to fuel cell sensors, it is envisioned that other types of sensors and other methods of evaluating the blood-alcohol content (BAC) of a sample of alveolar air may also be used in conjunction with the breath chamber assembly 50. A second opening 66 in housing 52 fluidly connects the breath chamber to alcohol sensor 60. A breath sample flows through second opening 66 to alcohol sensor 60 to facilitate the analysis of the alcohol content of the sample. A frame 62 is located on the outer surface of housing 52. An audio detector 64 is mounted in frame 62 for detecting sound waves produced in conjunction with the expiration of a breath sample, as will be described in more detail below.

Breath chamber assembly 50 includes one or more source evaluator components for measuring characteristics of an intake breath sample. These source evaluator components measure air sample characteristics as the sample is blown into the intake and through the breath chamber, before exiting the back of the chamber. The air sample characteristics are measured to aid in determining the source and validity of the sample. In particular, the source evaluator components sense or measure characteristics of an air sample for analyzing whether the sample is valid and from the designated human tester 16. Measurements from the source evaluator components are input to the processor 40, which is programmed to compare the measurements and sensed characteristics to a range of acceptable levels to determine the validity and source type of the sample. The processor 40 can invalidate the air sample, and lock out the vehicle ignition, if the measured characteristics indicate a non-human or fraudulent sample.

The source evaluator components include a temperature measuring device 70 and a heating element 72 which are integrated into the breath chamber cavity 54. In cold temperature environments, such as northern climates in the winter, the heating element 72 operates in conjunction with the temperature measuring device 70 to warm chamber 54 to near the typical human breath temperature range of 33-36° C. The temperature measuring device 70 provides temperature feedback to processor 40 to drive operation of the heating element 72 and control the temperature in the chamber. Heating element 72 warms the chamber 54 when device 12 is initially activated for receipt of a breath sample. Warming chamber 54 prevents breath moisture condensation when a warm breath sample is blown into a cold or sub-freezing breath chamber.

Figure 3:
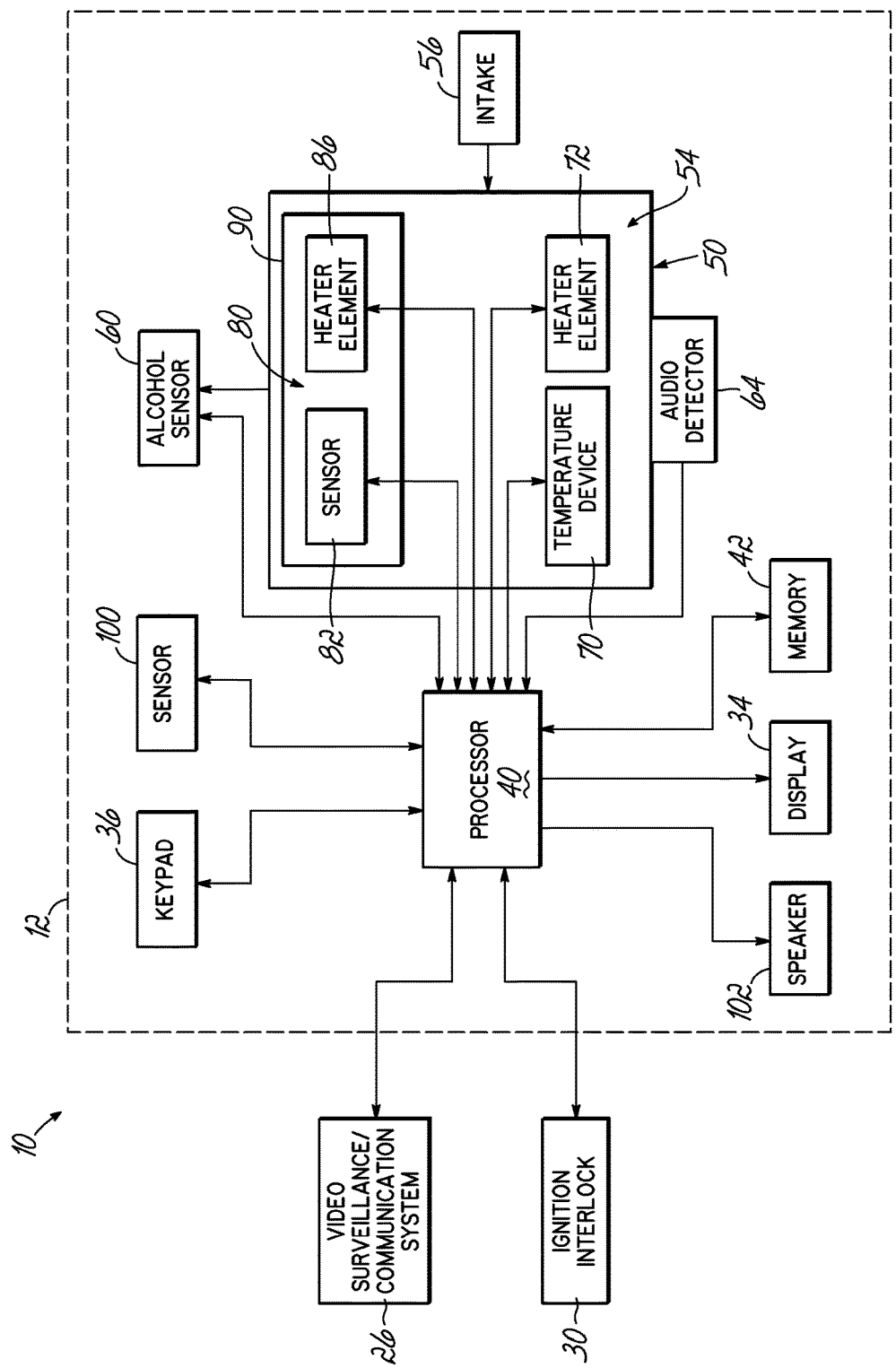
FIG. 3 is a block diagram of an embodiment of the chemical impairment detection system of FIG. 1.
Figure 4:
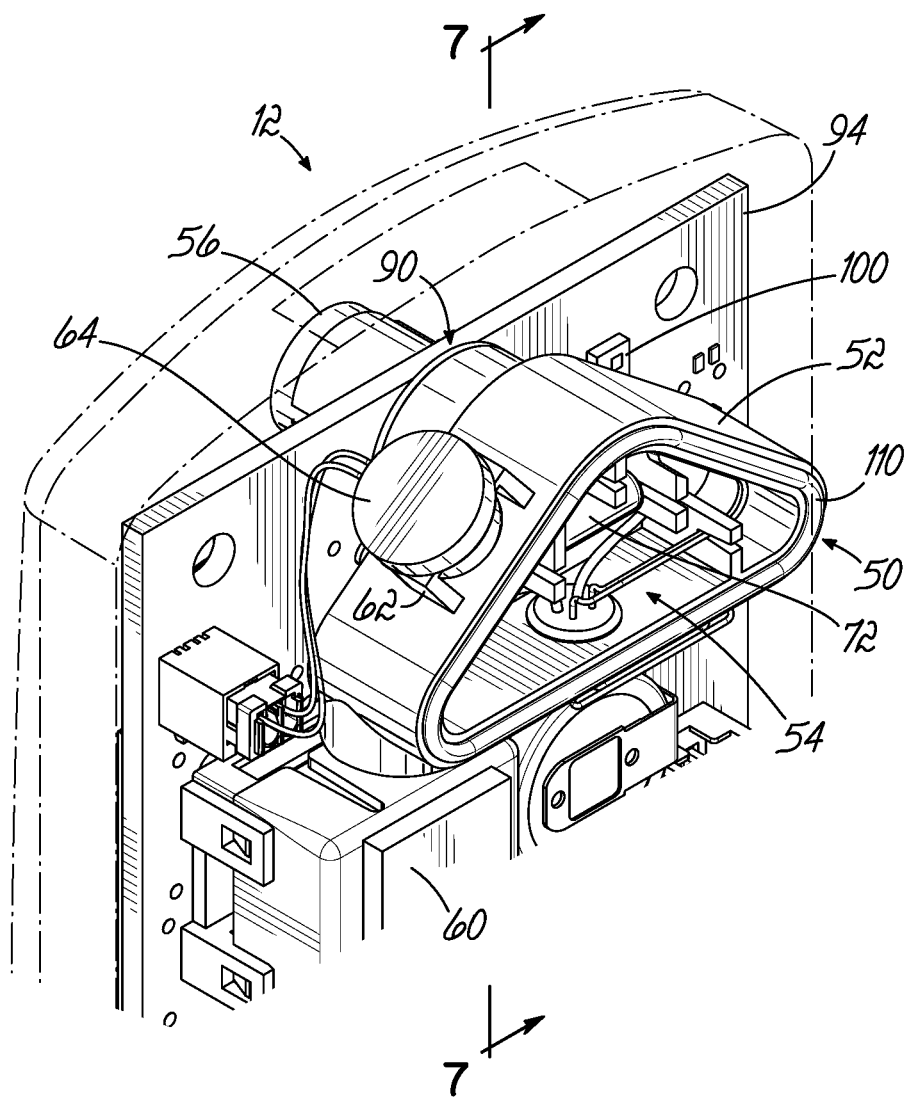
FIG. 4 is an isometric view of a portion of the hand-held device of FIG. 2, with the back panel removed to show the breath chamber.

When device 12 is operated in a more temperate environment, temperature measuring device 70 may be used to measure or sense the temperature of a breath sample blown into chamber cavity 54. The sensed temperature is communicated to processor 40, as shown in FIG. 3. Processor 40 can compare the sensed temperature with the normal range of human breath temperature of approximately 33-36° C. When the sensed breath sample temperature is moving away from human breath temperature, the processor may flag the breath sample as being fraudulent. The processor 40 can then transmit a signal to the vehicle ignition system 30 to disable operation of the vehicle, or otherwise communicate that the breath sample is invalid. Temperature measuring or sensing device 70 may, for example, be a thermistor. Alternatively, device 70 can be a Micro-Electromechanical System (MEMS) IR temperature sensor, or any other type of temperature sensing or measuring device known in the art. Additionally, heating element 72 can be a resistor, heating strip, or any other device capable of providing heat inside breath chamber cavity 54.

Figure 7:
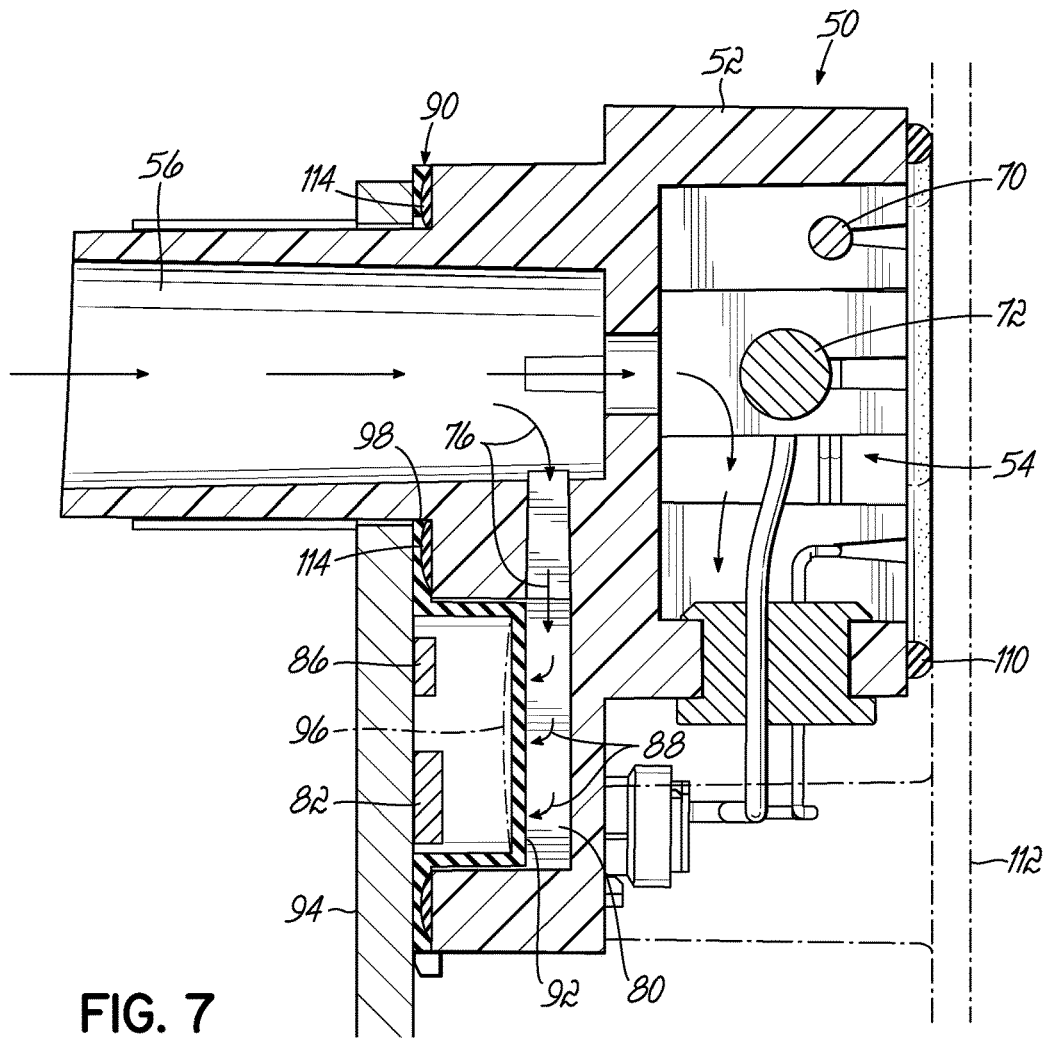
FIG. 7 is a sectional view of a portion of the hand-held device of FIG. 2, taken along line 7-7 in FIG. 4.
Figure 8:
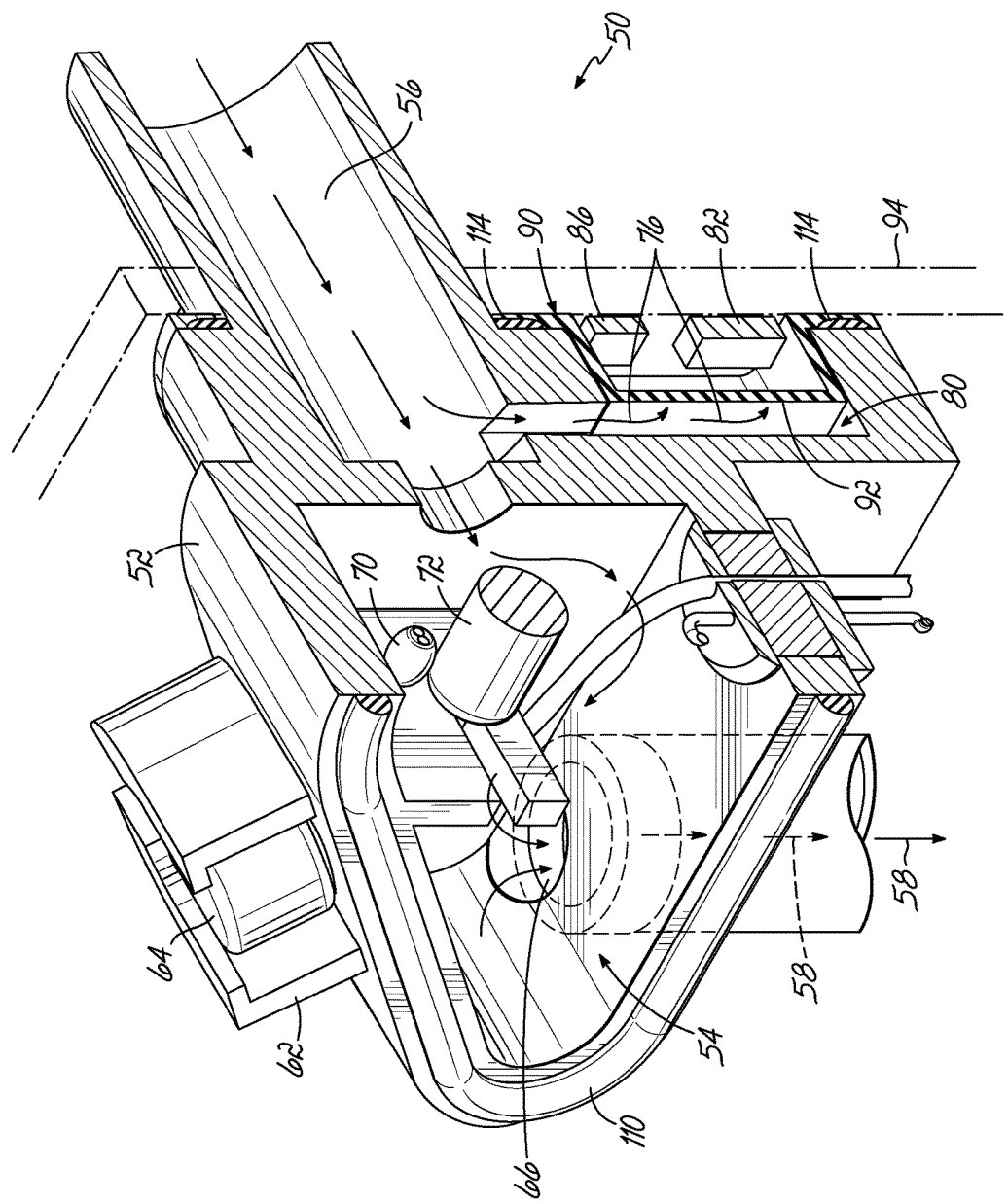
FIG. 8 is an isometric, sectional view of an exemplary breath chamber assembly for the hand-held device of FIG. 2, with the printed circuit board of the handset shown in phantom.

Breath chamber assembly 50 also includes integrated pressure sensing components for measuring air pressure in the breath chamber 54 as a breath sample is exhaled into the chamber, in order to calculate the tester breath flow rate. The breath flow rate is evaluated over a period of time, such as a breath sample window, to calculate the breath sample volume. As shown in FIGS. 3 and 7-8, the pressure sensing components are located in an area 80 of the breath chamber. Area 80 is fluidly connected to the remainder of the chamber cavity 54, so that as a breath sample enters and fills the chamber cavity, the air also expands within and fills area 80, as shown by arrows 76 in FIGS. 7 and 8. The pressure sensing components include a pressure sensor 82 and a heating element 86. In a preferred embodiment, pressure sensor 82 is a Micro-Electromechanical System (MEMS) piezo-resistive absolute pressure sensor. In the MEMS sensor, the sensing element is a suspended membrane that can sense absolute pressure and can sense temperature. In some embodiments, the sensor 82 will also sense relative humidity. MEMS pressure sensor 82 is mounted on a printed circuit board (PCB) 94 within device 12, as shown in FIG. 5, for communicating the measured pressure directly to processor 40.

A sealing member, such as a gasket 90, separates the pressure sensing components from the sample air in breath chamber area 80. Gasket 90 includes a box-like configuration 92 at one end for encasing the pressure sensing components between the gasket and the PCB 94. In addition, PCB 94 is designed to eliminate vias beneath gasket box 92 to prevent sample or ambient air from contacting the pressure sensing components, thereby providing an air-tight operating environment for pressure sensor 82 beneath gasket 90. The MEMS sensor 82 includes an internal temperature sensor which measures the temperature inside gasket box 92. Heating element 86 is encased with pressure sensor 82 inside gasket box 92 to provide a consistent temperature within the sealed compartment. Heating element 86 is regulated by processor 40 to turn on and off as needed to maintain the temperature in the sealed compartment above approximately 10° C. If the temperature falls below approximately 10° C., as measured by an internal temperature sensor in pressure sensor 82, processor 40 energizes heating element 86. The temperature beneath gasket box 92 is regulated to maintain the accuracy and linear performance of pressure sensor 82. Gasket 90 prevents any of the breath sample air and/or moisture from condensing on or affecting operation of the pressure sensing components.

Gasket 90 is composed of a flexible material, such as silicone, which is designed to be responsive to air pressure introduced into chamber 54 by an exhaled breath sample. In particular, as sample air is exhaled into chamber 54, the air enters area 80, as shown in FIGS. 7 and 8, increasing the pressure therein. As the air pressure increases, the surface pressure on gasket box 92 increases, as indicated by arrows 88 in FIG. 7, causing the upper surface of the box to depress in a responsive manner above the pressure sensing components, as indicated by the dashed line 96. The depression of the outer surface of gasket box 92 compresses the air molecules within the sealed box, which is sensed and measured as a pressure change by pressure sensor 82. The pressure change is communicated by sensor 82 to processor 40. Gasket 90 also includes an opening 98 that surrounds the sample intake opening 56.

Figure 5:
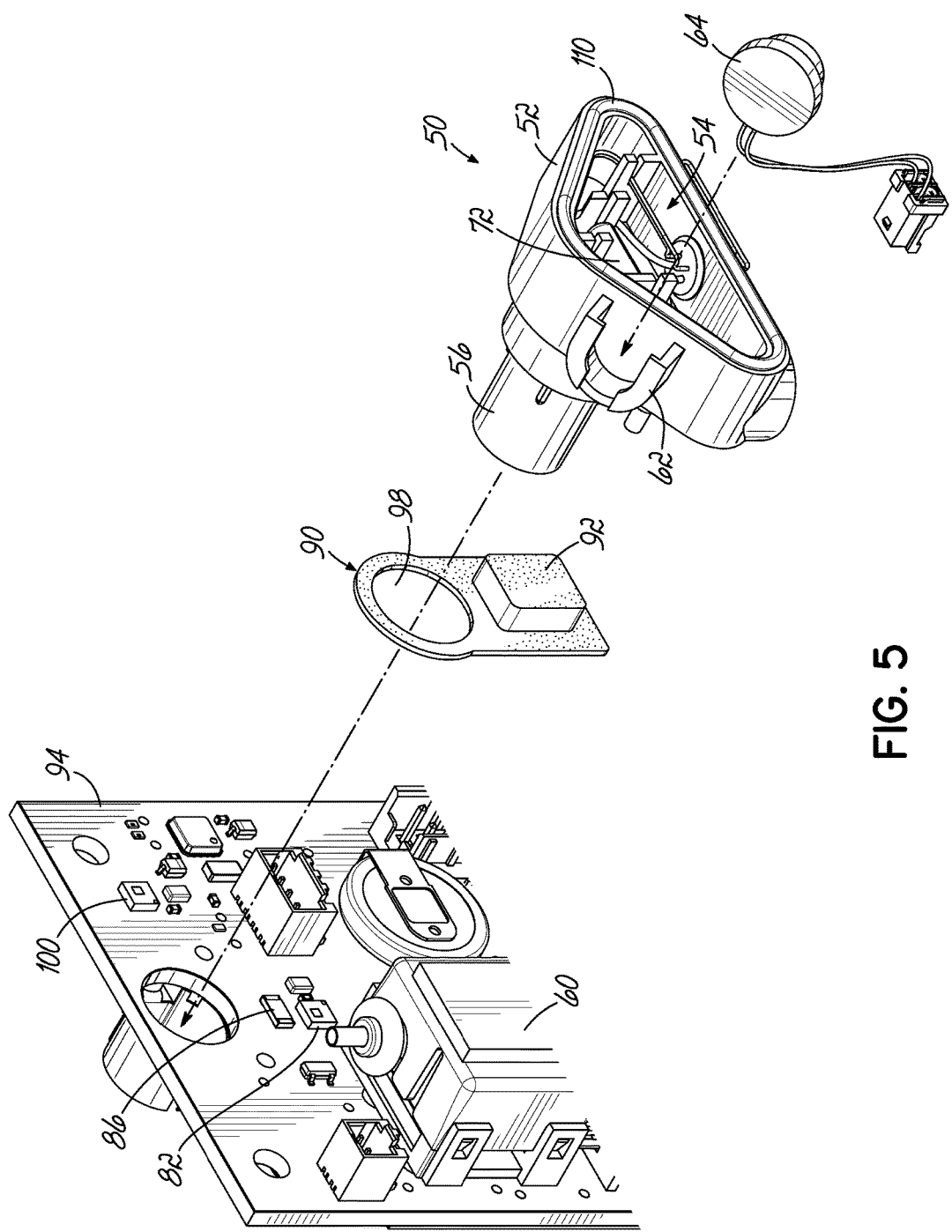
FIG. 5 is a partially exploded view of the hand-held device portion shown in FIG. 4.
Figure 6:
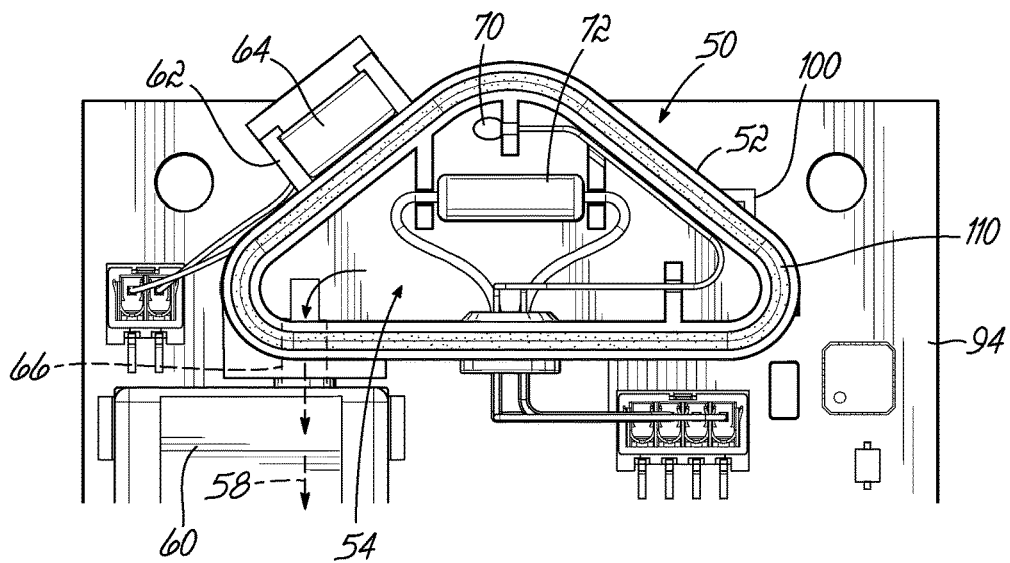
FIG. 6 is a back view of an upper portion of the hand-held device of FIG. 2, shown with the rear case enclosure removed.

As shown in FIGS. 5 and 6, a second pressure sensor 100 is mounted on PCB 94 outside of chamber 54. This second pressure sensor is preferably also a MEMS piezo-resistive absolute pressure sensor that is matched to the first pressure sensor 82. Second pressure sensor 100 measures ambient pressure and temperature within the hand-held device 12. In some embodiments, second pressure sensor 100 will also measure relative humidity. The ambient pressure measured by pressure sensor 100 is compared with the pressure measured by the first pressure sensor 82 to calculate the positive differential pressure of the air sample entering breath chamber cavity 54. Processor 40 uses the positive differential pressure during the intake period of the breath sample to calculate the volume of the breath sample. Processor 40 then determines whether the breath sample volume meets the minimum standard required by law, as programmed into the device 12. When the minimum air volume has been achieved for the test to be considered valid, the processor 40 can communicate this status to the tester 16 through display 34 or audibly, such as by initiating or terminating a sound from speaker 102. If the minimum breath sample volume is not achieved during a testing time window, which is typically approximately 5 seconds, the processor 40 will generate an invalid signal to flag the sample as invalid. The tester 16 may then be prompted to exhale a second air sample into device 12, and/or operation of the vehicle may be prevented until such time as a valid air sample is input to the device 12.

Figure 9:
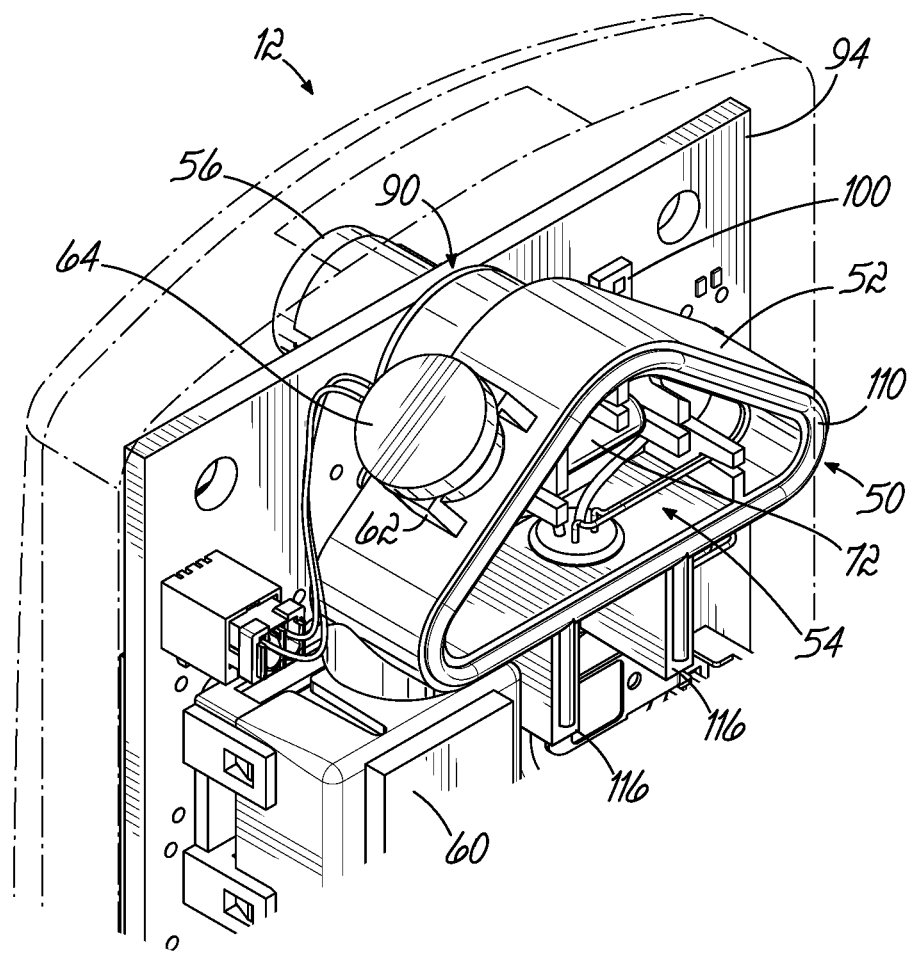
FIG. 9 is an isometric view similar to FIG. 4, showing an alternative embodiment for the breath chamber assembly.
Figure 11:
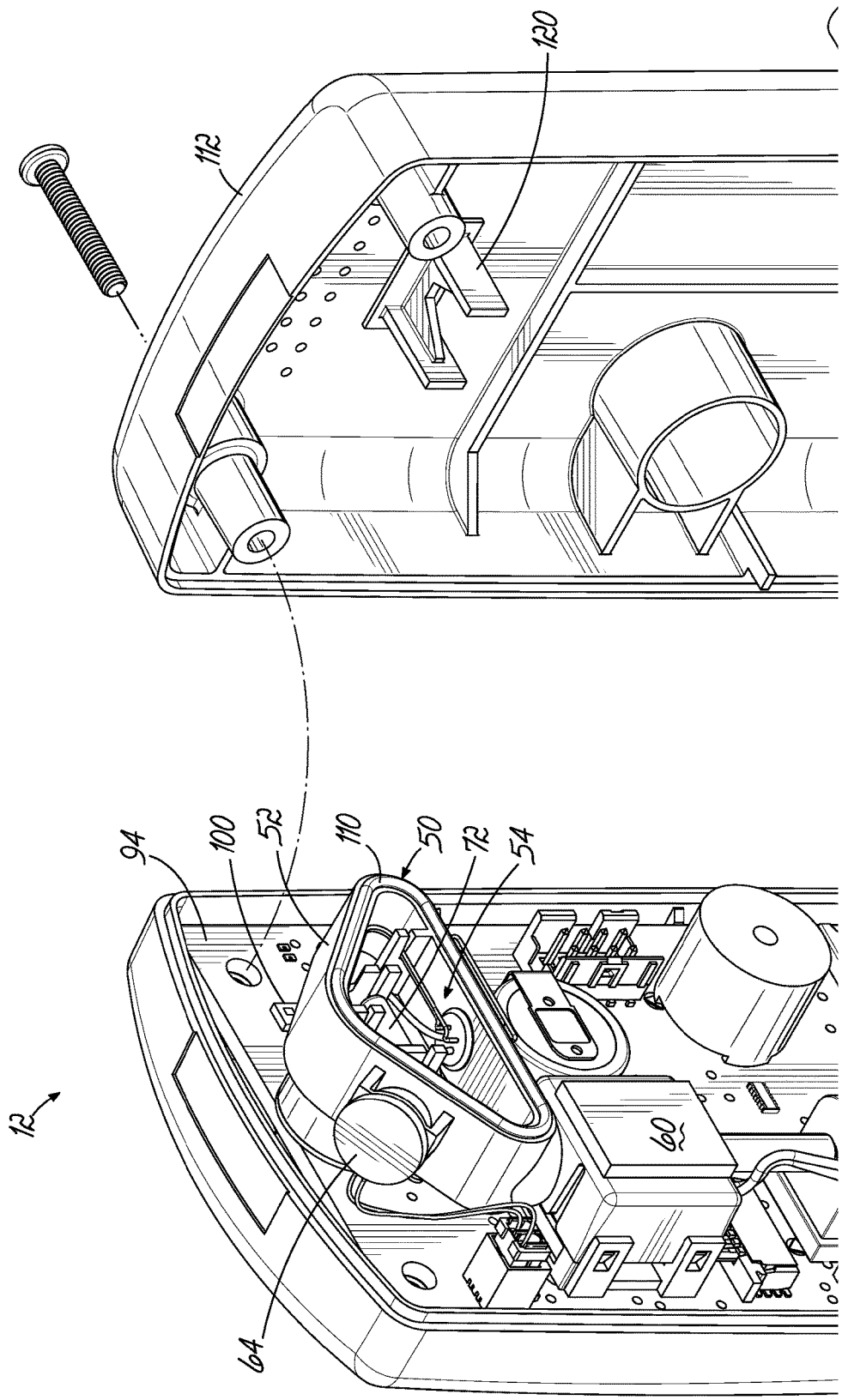
FIG. 11 is a partial, isometric view of the hand-held device shown with the back panel pulled away from the device.
Figure 12:
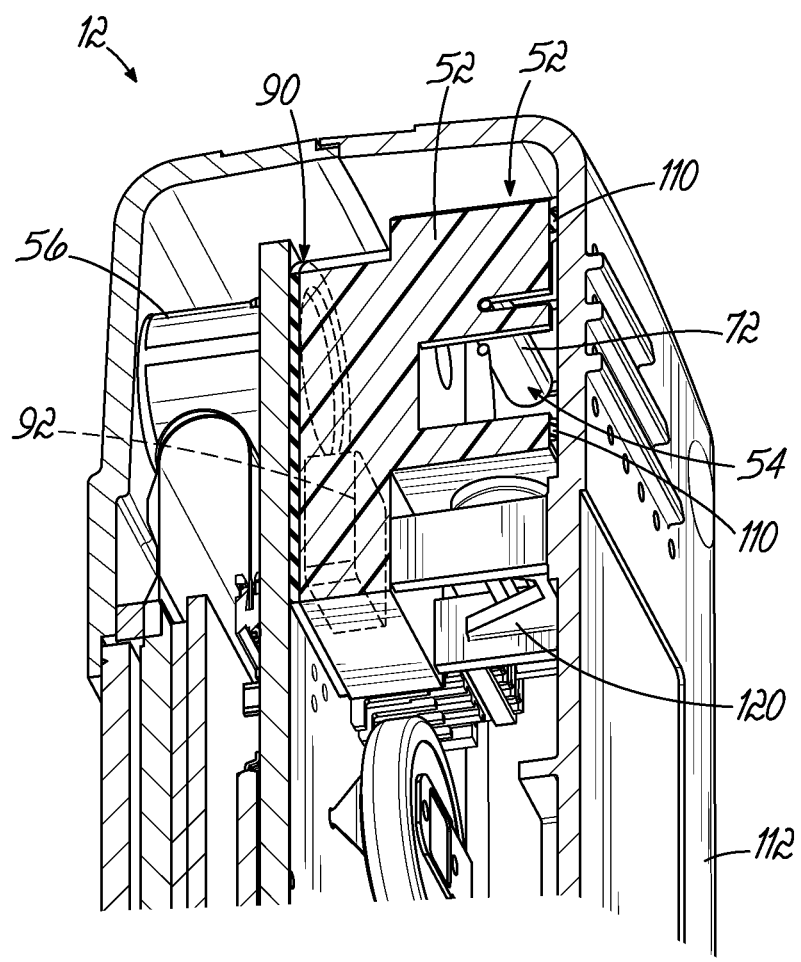
FIG. 12 is a partial, sectional view of the hand-held device.

An additional sealing member, which can be in the form of an over-molded edge 110, is provided around the perimeter of breath chamber housing 52 to provide an air and moisture seal between the chamber 54 and a rear device panel 112. The over-molded edge 110 can be composed of a thermoplastic elastomer or other similar flexible sealing material. A second sealing member 114, which can also be in the form an over-molded edge, extends around the perimeter of the opposite side of chamber housing 52. Second edge seal 114 provides a seal between the chamber cavity 54 and the circuit board 94. The sealing members 110, 114 prevent air that is blown into the device 12 from leaking outside of the breath chamber assembly 50, or being diverted into the printed circuit board area. Sample air is confined within the chamber cavity 54, and expands within the sealed chamber, before exiting the chamber through vent holes (not shown) in the rear case enclosure 112. FIG. 9 depicts an alternative embodiment for the breath chamber assembly in which additional brackets with sealing members, identified at 116, extend from the breath chamber housing 52. Using the sealing edges to confine the air sample to chamber 54 as the sample flows from the intake, into the chamber, and then exits through the rear case, prevents sample condensation from impacting electronic components in other parts of the device 12, thereby avoiding the need to apply a protective coating to the printed circuit boards and other components to protect the components from damage due to breath sample condensation. As shown in FIG. 11 and FIG. 12, device 12 can include a bracket 120 extending from rear case panel 112 into contact with the exterior of breath chamber housing 52 over area 80. The contact of bracket 120 against housing 52 facilitates a fluid tight seal between sealing member 90 and PCB 94.

As mentioned above, breath chamber assembly 50 further includes an audio detector 64 mounted on the exterior of housing 52 for detecting and measuring characteristics of sound waves produced in conjunction with a breath sample. The audio detector 64 may be a unidirectional microphone mounted in frame 62, with the face of the microphone contacting or in close proximity to the outer surface of housing 52. The microphone is mounted in this manner to detect a hum sound as tester 16 exhales into chamber 54. Mounting the face of the microphone against housing 52 limits the impact of outside ambient noise on the microphone reception. As a tester 16 hums and blows into device 12, the vibration of the hum is transmitted into breath chamber 54. The vibration is measured by the microphone, which generates a signal that is amplified and transmitted to processor 40. Processor 40 receives the hum signal from the microphone, and analyzes the amplitude and frequency of the signal, to validate the air sample source as originating from a human as opposed to a forced air source. In addition to a condenser microphone, audio detector 64 could also be a MEMS microphone. The pressure changes can be measured and analyzed by processor 40 to validate the tester's 16 hum.

After processor 40 analyzes the breath sample volume, temperature and/or hum associated with a breath sample, the processor can determine whether the sample is a valid sample. If the sample is valid, the processor 40 can interpret the alcohol measurement from alcohol sensor 60. If the measured alcohol level is below the threshold designated by the laws in the state in which the test is being conducted, the processor 40 can communicate the successful test either audibly or visually to the tester 16. Additionally, the processor 40 may log the test result in device memory 42 and/or communicate the test result to an external facility through system 26. If the processor 40 determines that the breath sample is invalid, the processor 40 may prompt the user 16 for a second sample, as described above, or flag the sample as invalid. The invalid sample may be logged in device memory 42, and communicated to the tester 16 and an external facility using system 26. Additionally, upon detection of an invalid sample, processor 40 may communicate with ignition interlock 30 to lock out the vehicle ignition, or otherwise prevent operation of the vehicle.

Figure 10:
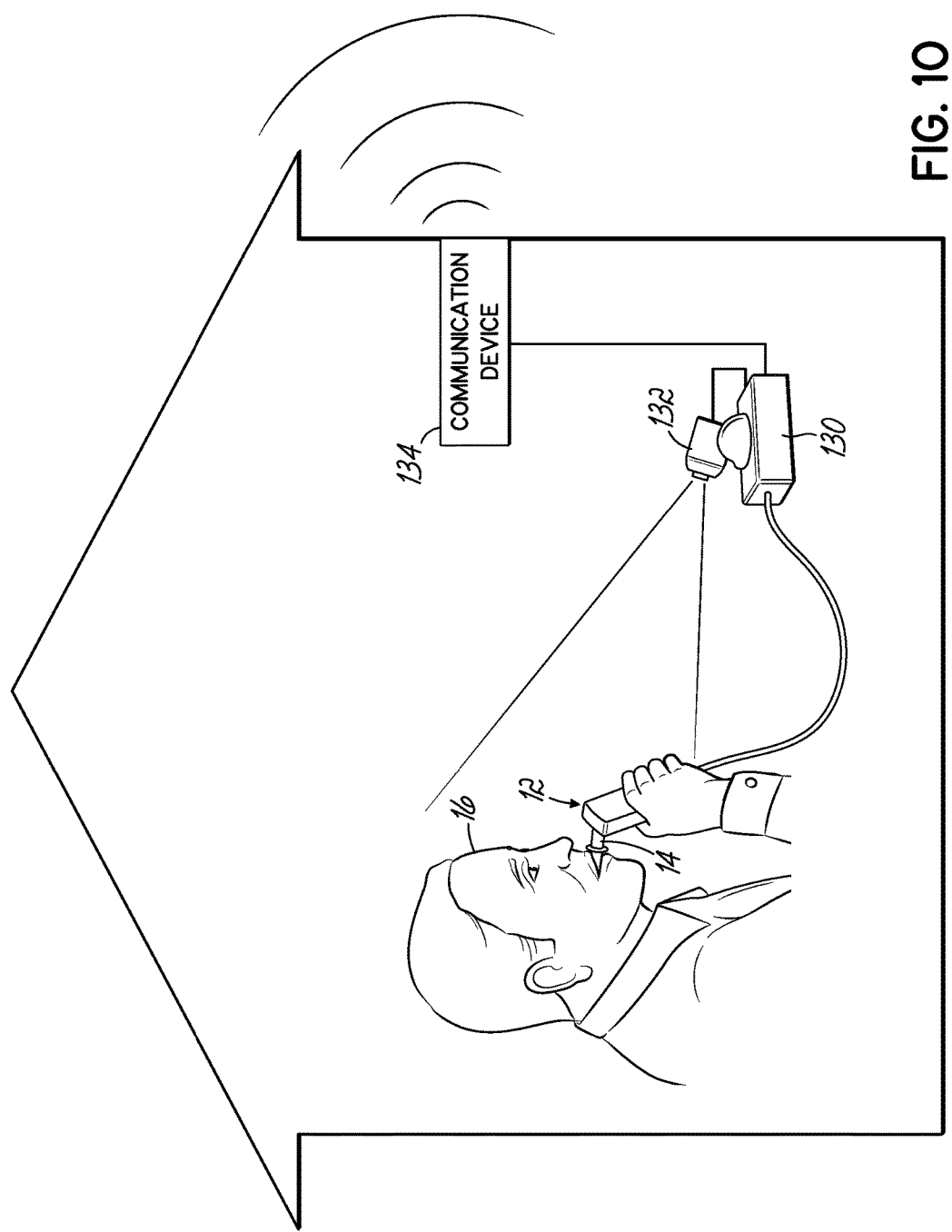
FIG. 10 is a diagrammatic view of a non-vehicular embodiment of a chemical impairment detection system.

FIG. 10 depicts an alternative, non-vehicular application of chemical impairment detection system 10. In this application, system 10 is used outside of a vehicle, such as within the home of an impairment tester 16 or other non-mobile facility. System 10 can be used in this scenario as part of a home monitoring or incarceration program. In this application, system 10 includes a hand-held device 12, similar to that described above, for intake and evaluation of a tester's breath sample. Hand-held device 12 is attachable to a control unit 130 resident in the home or other non-vehicular location. Hand-held device 12 can be removably attached to the control unit 130 to enable the same hand-held device to be operated with both a vehicle-based control module 20 and with the home-based control unit 130. Control unit 130 can serve as a base cradle for the hand-held device 12. Control unit 130 includes either an internal power supply or, alternatively, a connector for accessing an external power supply. Control unit 130 can connect to a video surveillance system 132 for capturing and recording one or more images of the tester 16 during input of a breath sample to hand-held device 12. Control unit 130 also incorporates, or is connected to, a communication device 134. Communication device 134 can include a wired or wireless communication transceiver for enabling two-way communication with a monitoring facility. Communication device 134 can operate in a manner similar to that described above for system 26, in order to communicate with an external facility to allow a request for a breath sample test, facilitate transfer of test results to an external facility, direct an override, lockout or bypass of system 10, or otherwise provide for communication with the tester 16 or system 10. Control unit 130 may also include GPS capability to enable verification of the control unit's location during an alcohol test. Alternatively, a cellular connection between communication device 134 and a cellular communication tower can be utilized to determine the location of the control unit 130 at the time of an alcohol test.

The foregoing has described a multi-functional breath chamber assembly for an impairment detection device in which the volume of a breath sample can be determined using components incorporated into the breath chamber. By incorporating the air sample sensing components into the breath chamber, the assembly described herein eliminates the need to transfer an air sample within the device. Breath sample air passes directly from the intake opening, through the breath chamber, and out vent holes in the rear panel of the device. Additionally, anti-circumvention features, including temperature and hum sensing, are integrated into the breath chamber. The breath chamber may be warmed prior to receiving a breath sample, and the breach chamber sealed off from the remainder of the device, to reduce or eliminate breath condensation within the device. Warming the breath chamber prior to intake of a breath sample also prevents breath condensation from impacting the alcohol sensor or blocking the intake to the alcohol sensor.

The present invention has been described in connection with several embodiments and some of those embodiments have been elaborated in substantial detail. However, the scope of the invention is not to be limited by these embodiments which are presented as exemplary and not exclusive. The scope of the invention being claimed is set forth by the following claims.

What is claimed is:

1. A chemical impairment detection system comprising:
an intake adapted to receive an air sample from a source;
an alcohol sensor for detecting an alcohol level in the air sample;
an integrated breath chamber for channeling the air sample from the intake to the alcohol sensor, wherein the integrated breath chamber is comprised of an internal cavity and an external shell;
a source evaluator means in the integrated breath chamber for measuring one or more characteristics of the received air sample for validating the air sample, the source evaluator means measuring characteristics of the air sample as the air sample flows through the integrated breath chamber,
wherein the source evaluator means comprises a temperature measuring device and a heating element located in the internal cavity of the integrated breath chamber, and wherein the source evaluator means further comprises a pressure sensing means located in the internal cavity of the integrated breath chamber for measuring pressure of the air sample; and
a second pressure sensor located outside of the integrated breath chamber.

2. The chemical impairment detection system of claim 1, further comprising a processor for analyzing one or more characteristics of the received air sample and disabling operation of a vehicle when the received air sample is determined to be invalid.

3. The chemical impairment detection system of claim 1, wherein the temperature measuring device measures a temperature of the air sample within the internal cavity of the integrated breath chamber, and the source evaluator means further comprises a processor for comparing the measured air sample temperature with an acceptable range of human breath temperature.

4. The chemical impairment detection system of claim 3, wherein the processor compares the measured air sample temperature with an acceptable range of human breath temperature and disables operation of a vehicle when the air sample is determined to be invalid.

5. The chemical impairment detection system of claim 3, wherein the heating element is driven by the processor based on a measured air temperature from the temperature measuring means.

6. The chemical impairment detection system of claim 1, wherein the source evaluator means further comprises a processor for determining an air sample volume from the measured air sample pressure, the processor comparing the air sample volume to an acceptable minimum volume to determine validity of the air sample.

7. The chemical impairment detection system of claim 6, wherein the processor invalidates the air sample when the air sample volume is less than an acceptable minimum volume.

8. The chemical impairment detection system of claim 6, wherein the pressure sensing means further comprises a Micro-Electromechanical System pressure and temperature sensor which digitally communicates the measured pressure of the air sample to the processor.

9. The chemical impairment detection system of claim 8, further comprising a sealing member in the breath chamber separating the pressure and temperature sensor from the air sample.

10. The chemical impairment detection system of claim 9, wherein the sealing member flexes in response to pressure from the air sample in the breath chamber, and wherein the pressure sensor measures a pressure change produced by the flexing sealing member and outputs the pressure change to the processor for calculating the air sample volume.

11. The chemical impairment detection system of claim 1, wherein the source evaluator means further comprises an audio detector on the external shell of the integrated breath chamber for measuring characteristics of sound waves associated with the air sample.

12. The chemical impairment detection system of claim 11, wherein the audio detector further comprises a microphone for detecting a hum signal associated with the intake of the air sample.

13. A chemical impairment detection system comprising:
an intake adapted to receive an air sample from a source;
an alcohol sensor for detecting an alcohol level in the air sample;
an integrated breath chamber for channeling the air sample from the intake to the alcohol sensor, wherein the integrated breath chamber is comprised of an external shell and an internal cavity;
a source evaluator means in the integrated breath chamber for measuring one or more characteristics of the received air sample for validating the air sample, the source evaluator means measuring characteristics of the air sample as the air sample flows through the integrated breath chamber, wherein the source evaluator means comprises a temperature measuring device and a heating element located in the internal cavity of the integrated breath chamber, wherein the source evaluator means further comprises a pressure sensing means located in the internal cavity of the integrated breath chamber for measuring pressure of the air sample, and a processor for determining an air sample volume from the measured air sample pressure, the processor comparing the air sample volume to an acceptable minimum volume to determine validity of the air sample, and wherein the pressure sensing means further comprises a Micro-Electromechanical System pressure and temperature sensor which digitally communicates the measured pressure of the air sample to the processor; and
a second pressure sensor located outside of the integrated breath chamber for measuring pressure and temperature outside of the integrated breath chamber, the pressure sensing means within located in the integrated breath chamber and the second pressure sensor located outside of the integrated breath chamber combining to provide differential pressure and temperature measurements of the air sample.

14. An integrated breath chamber assembly for an alcohol impairment detection device having an air sample intake and an alcohol sensor, the assembly comprising:
a breath chamber housing further comprising an internal cavity and an external shell, the internal cavity formed therein for receiving and evaluating an air sample, the internal cavity extending between the intake and the alcohol sensor for channeling an air sample from the intake to the alcohol sensor;
a temperature measuring device and a heating element located in the internal cavity of the breath chamber;
a pressure sensing means located in the internal cavity of the breath chamber for measuring pressure of the air sample in the internal cavity;
a second pressure sensor located outside of the breath chamber; and
a processor for calculating an air sample volume from the measured air pressure, the processor invalidating the air sample if the calculated air sample volume is below a minimum threshold volume.

15. The integrated breath chamber assembly of claim 14, further comprising an audio detector located on the external shell of the breath chamber for detecting sound waves associated with the air sample, the processor analyzing the detected sound waves to validate the air sample.

16. The integrated breath chamber assembly of claim 14, wherein the pressure sensing means further comprises a Micro-Electromechanical System pressure sensor.

17. The integrated breath chamber assembly of claim 16, further comprising a sealing member for separating the pressure sensing means from the air sample in the breath chamber.

18. The integrated breath chamber assembly of claim 17, wherein the sealing member flexes in response to pressure from the air sample in the breath chamber, and wherein the pressure sensing means measures a change in pressure produced by the flexing sealing member and outputs the pressure change to the processor for calculating the volume of the air sample.

19. The integrated breath chamber assembly of claim 14, wherein the heating element is driven by the processor based on measured air temperature from the temperature measuring means.

20. The integrated breath chamber assembly of claim 14, wherein the breath chamber housing further comprises flexible sealing members for isolating the air sample within the cavity.

21. A chemical impairment detection device comprising:
an intake adapted to receive an air sample from a source;
an alcohol sensor for detecting an alcohol level in the air sample;
an integrated breath chamber for receiving the air sample and channeling the air sample from the intake to the alcohol sensor, the breath chamber further comprising an internal cavity and an external shell, the breath chamber including a temperature measuring device located in the internal cavity of the breath chamber for measuring temperature in the breath chamber, a heating element located in the internal cavity of the breath chamber, a pressure sensing means located in the internal cavity of the breath chamber for measuring the pressure of the air sample, and an audio detector located on the external shell of the breath chamber for detecting sound waves associated with the air sample;
a second pressure sensor located outside of the breath chamber; and
a processor for receiving signals from one or more of the temperature sensing means, pressure sensing means, and audio detector, and determining validity of the air sample.

22. The chemical impairment detection device of claim 21, wherein the heating element is driven by the processor based on measured air temperature from the temperature measuring means.

23. The chemical impairment detection device of claim 21, wherein the pressure sensing means further comprises a Micro-Electromechanical System pressure sensor.

24. The chemical impairment detection device of claim 23, further comprising a sealing member for separating the pressure sensor from the air sample in the breath chamber.

25. The chemical impairment detection device of claim 24, wherein the sealing member flexes in response to pressure from the air sample in the breath chamber, and wherein the pressure sensor measures a change in pressure produced by the flexing sealing member and outputs the pressure change to the processor for calculating a volume of the air sample.

26. The chemical impairment detection device of claim 21, wherein the chemical impairment detection device is utilized within a vehicle, and the processor disables operation of the vehicle when the received air sample is determined to be invalid.

27. The chemical impairment detection device of claim 21, wherein the chemical impairment detection device is utilized within a home as part of a home monitoring program.

* * * * *

UNITED STATES PATENT AND TRADEMARK OFFICE
CERTIFICATE OF CORRECTION

PATENT NO. : 10,488,398 B2
APPLICATION NO. : 14/973275
DATED : November 26, 2019
INVENTOR(S) : Nicholas M. Trainor et al.

Page 1 of 1

It is certified that error appears in the above-identified patent and that said Letters Patent is hereby corrected as shown below:

In the Specification

Column 8, Line number 48, reads "... in the form an over-molded edge, ..." but should read "... in the form of an over-molded edge, ..."

Signed and Sealed this
Fifth Day of May, 2020

Andrei Iancu
*Director of the United States Patent and Trademark Office*